(12) United States Patent
O'Hare

(10) Patent No.: US 11,975,184 B2
(45) Date of Patent: May 7, 2024

(54) TRAINING DEVICE FOR DEFIBRILLATORS

(71) Applicant: HeartSine Technologies Limited, Belfast (GB)

(72) Inventor: Peter O'Hare, Belfast (GB)

(73) Assignee: HEARTSINE TECHNOLOGIES LIMITED, Belfast (GB)

( * ) Notice: Subject to any disclaimer, the term of this patent is extended or adjusted under 35 U.S.C. 154(b) by 1078 days.

(21) Appl. No.: 16/219,405

(22) Filed: Dec. 13, 2018

(65) Prior Publication Data

US 2019/0192845 A1 Jun. 27, 2019

(30) Foreign Application Priority Data

Dec. 22, 2017 (GB) ..................................... 1721797

(51) Int. Cl.
*A61N 1/04* (2006.01)
*A61N 1/39* (2006.01)
*G09B 23/28* (2006.01)
*G09B 23/30* (2006.01)

(52) U.S. Cl.
CPC .......... *A61N 1/0408* (2013.01); *A61N 1/3925* (2013.01); *G09B 23/288* (2013.01); *A61N 1/3904* (2017.08); *A61N 1/3993* (2013.01); *G09B 23/30* (2013.01)

(58) Field of Classification Search
CPC ...... G09B 23/288; G09B 23/30; G09B 23/28; A61N 1/0408; A61N 1/3993; A61N 1/3904; A61N 1/3925; A61N 1/04
USPC ......................................................... 434/265
See application file for complete search history.

(56) References Cited

U.S. PATENT DOCUMENTS

2018/0161587 A1\* 6/2018 Beyer ...................... A61N 1/18
2018/0374391 A1\* 12/2018 Lint ...................... A61N 1/3993

\* cited by examiner

*Primary Examiner* — Timothy A Musselman

(57) ABSTRACT

A training device for training a trainee to operate a defibrillator including a housing having a shape which imitates a shape of a defibrillator, a defibrillator function emulation device attached to the housing and configured to emulate a predefined subset of functions of a defibrillator, and electrodes attached to the housing. The trainer defibrillator of the disclosure simulates a real defibrillator, but, due to limited functionality and construction, will be much less expensive than existing trainer defibrillators and will therefore be able to be distributed more widely.

20 Claims, 1 Drawing Sheet

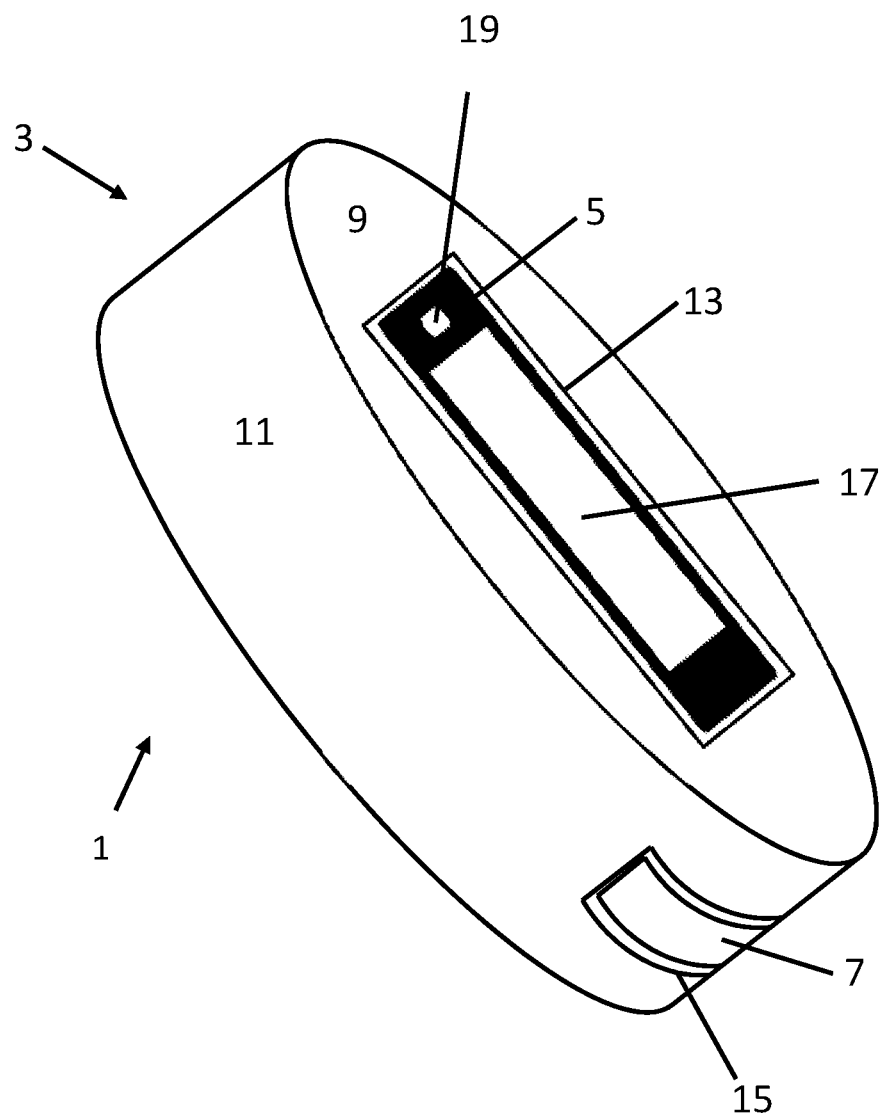

TRAINING DEVICE FOR DEFIBRILLATORS

PRIORITY INFORMATION

The present application claims priority to United Kingdom application No. 1721797.7, filed 22 Dec. 2017, the contents of which is incorporated herein by reference in its entirety.

BACKGROUND OF THE INVENTION

1. Field of the Invention

The disclosure relates to training devices for defibrillators and particularly to training devices which are easy and inexpensive to manufacture.

2. Introduction

Training in the use of defibrillators is becoming increasingly important, as defibrillators are being placed in more and more locations. However, trainer defibrillators which are commonly used are based on defibrillators with some functionality, such as defibrillation shock production, disabled. As such, trainer defibrillators include all or most of the components of defibrillators, they can be expensive, which limits their availability.

SUMMARY

Additional features and advantages of the disclosure will be set forth in the description which follows, and in part will be obvious from the description, or may be learned by practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth herein.

According to a first aspect of the disclosure, there is provided a training device for training a trainee to operate a defibrillator. The training device includes a housing having a shape which imitates a shape of a defibrillator, a defibrillator function emulation device attached to the housing and configured to emulate a predefined subset of functions of a defibrillator, and electrodes attached to the housing.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only exemplary embodiments of the disclosure and are not therefore to be considered to be limiting of its scope, the disclosure will be described and explained with additional specificity and detail through the use of the accompanying drawings in which:

FIG. 1 illustrates a training device as disclosed herein.

DETAILED DESCRIPTION

Disclosed is a training device 1 that includes a housing 3 having a shape which imitates a shape of a defibrillator, a defibrillator function emulation device 5 attached to the housing and configured to emulate a predefined subset of functions of a defibrillator, and electrodes 7 attached to the housing.

The training device 1 emulates only a predefined subset of functions of a defibrillator and some functionality, such as defibrillation shock production, is not provided. The training device therefore does not have to comprise all or most of the components of a defibrillator and can therefore be relatively low cost.

The housing 3 can include any of a cardboard structure, a plastic structure, a polystyrene structure, a foam structure, a polymer foam structure. The housing is made of an inexpensive material, such as cardboard or plastic, to provide the overall 3-dimensional form of the defibrillator and to reduce the cost of the training device.

The housing 3 can include a cylindrical shape. The cylindrical shape can include a first substantially oval face, a second substantially oval face and a wall therebetween. The cylindrical shape can include a first substantially circular face, a second substantially circular face and a wall therebetween. The cylindrical shape can include a first substantially square face, a second substantially square face and a wall therebetween. The cylindrical shape can include a first substantially rectangular face, a second substantially rectangular face and a wall therebetween. The cylindrical shape can include a first substantially polygonal face, a second substantially polygonal face and a wall therebetween. The housing can include a get-up which imitates a defibrillator. This, along with shape of the training device, will enhance the authenticity of a trainee's experience.

The housing 3 may provide at least one space for at least partial receipt of the defibrillator function emulation device for attachment of the device to the housing. The space may be provided in a face of a cylindrical housing. The space may be sized to form a fit around the defibrillator function emulation device. The housing can include one or more inserts to change the size of the space to accommodate differently-sized defibrillator function emulation devices. The space may comprise a recess for partial receipt of the defibrillator function emulation device. The space can include a slot for substantially full receipt of the defibrillator function emulation device.

The housing may provide at least one space for at least partial receipt of the electrodes 7 for attachment of the electrodes to the housing. The space may be provided in a wall of a cylindrical housing. The space may be provided in a face of a cylindrical housing. The space can include a recess for partial receipt of the electrodes. The space can include a slot for substantially full receipt of the electrodes. Providing a space which at least partially receives the electrodes, mimics the position of electrodes in an actual defibrillator and enhances the authenticity of a trainee's experience.

The housing 3 can include at least one lid movable between a closed position and an open position. The housing can include a lid movable between a closed position covering the defibrillator function emulation device and the electrodes and an open position revealing the defibrillator function emulation device and the electrodes. The housing can include a lid movable between a closed position covering the defibrillator function emulation device and an open position revealing the defibrillator function emulation device. The housing can include a lid movable between a closed position covering the electrodes and an open position revealing the electrodes.

The electrodes 7 may be emulation defibrillator electrodes. The electrodes may be defibrillator electrodes.

The defibrillator function emulation device 5 may be configured to emulate a predefined subset of functions of a defibrillator including one or more of a defibrillator activation function, a defibrillator status function, a defibrillator ECG measurement function, a defibrillator impedance measurement function, a defibrillator cardiac analysis function, a defibrillator cardiac diagnosis function, a defibrillator treatment function, a defibrillator user instruction function.

The defibrillator function emulation device 5 may run software that emulates the predefined subset of functions of a defibrillator. The defibrillator function emulation device can include a display screen to issue instructions and information to a trainee. The defibrillator function emulation device can include a speaker to issue instructions and information to a trainee. The defibrillator function emulation device can include a memory module configured to store details of use of the training device. The defibrillator function emulation device may be any of a smart phone, a tablet.

Referring again to FIG. 1, the training device 1 includes a housing 3, a defibrillator function emulation device 5 attached to the housing, and defibrillator electrodes 7 attached to the housing. In this embodiment, actual defibrillator electrodes are used, but it will be appreciated that emulation electrodes could be used.

The housing 3 includes a cardboard structure and has a cylindrical shape, which imitates the shape of a defibrillator, including a first substantially oval face 9, a second substantially oval face (not shown) and a wall 11 therebetween. In use, the first face 9 is a top face of the housing 3 and the second face is a bottom face of the housing 3. The shape may also be square, rectangular, box-shaped, arbitrarily-shaped, or other configurations.

The housing 3 provides a first slot 13 provided in the first face 9 of the housing 3. The slot is sized to form a fit around the defibrillator emulation device 5, as shown, for substantially full receipt of the device 5 to attach it to the housing 3.

The housing 3 provides a second slot 15 provided in the wall 11 of the housing 3. The second slot 15 substantially fully receives the defibrillator electrodes 7 for attachment of the electrodes 7 to the housing 3.

In this embodiment, the defibrillator function emulation device 5 includes a smart phone. It will be appreciated that other similar devices may be used. The defibrillator function emulation device 5 is configured to emulate a predefined subset of functions of a defibrillator. The defibrillator functions include one or more of a defibrillator activation function, a defibrillator status function, a defibrillator ECG measurement function, a defibrillator impedance measurement function, a defibrillator cardiac analysis function, a defibrillator cardiac diagnosis function, a defibrillator treatment function and a defibrillator user instruction function. The defibrillator function emulation device 5 includes a display screen 17 and a speaker 19 to issue instructions and information to a trainee using the training device 1.

In a first use scenario, a trainee is provided with the housing 3 and defibrillator electrodes 7 of the training device 1. The trainee places his or her smart phone in the slot 13 of the face 9 of the housing 3 and operates defibrillator function emulation software loaded on the phone as an app. The smart phone then acts as a defibrillator function emulation device and emulates functions of a defibrillator and issues instructions and information to the trainee. The trainee follows the instructions, including removal of the defibrillator electrodes 7 from the slot 15 of the trainer defibrillator 1, thus learning how to operate a defibrillator.

In an alternative use scenario, a trainee is provided with the housing 3, the defibrillator function emulation device 5 and defibrillator electrodes 7 of the training device 1. The trainee activates the defibrillator function emulation device 5 and follows instructions provided by the device, thus learning how to operate a defibrillator.

The training device of the disclosure simulates a real defibrillator, but will be much less expensive than existing trainer defibrillators and will therefore be able to be distributed more widely.

I claim:

1. A training device for training a trainee to operate a defibrillator comprising:
   a housing having a shape which imitates a shape of the defibrillator;
   a defibrillator function emulation device having at least a display screen to display first data and a speaker to issue second data, the defibrillator function emulation device attached to the housing in a space configured within the housing and configured to emulate via software simulation a predefined subset of functions of the defibrillator, wherein the housing comprises one or more inserts to change a size of the space to accommodate differently-sized defibrillator function emulation devices; and
   emulation electrodes attached to the housing, wherein the training device does not contain any component capable of being charged to provide a defibrillation shock, wherein the predefined subset of functions that are emulated comprise a defibrillator treatment function in which a shock production through the emulation electrodes is simulated.

2. A training device according to claim 1, in which the housing comprises any of a cardboard structure, a plastic structure, a polystyrene structure, a foam structure, a polymer foam structure.

3. A training device according to claim 1, in which the housing comprises one of a cylindrical shape, a rectangular shape or a box shape.

4. A training device according to claim 3, in which the housing comprises any of a first substantially oval face, a second substantially oval face and a wall therebetween, a first substantially circular face, a second substantially circular face and a wall therebetween, a first substantially square face, a second substantially square face and a wall therebetween, a first substantially rectangular face, a second substantially rectangular face and a wall therebetween, a first substantially polygonal face, a second substantially polygonal face and a wall therebetween.

5. A training device according to claim 1, in which the housing comprises a structure which imitates the defibrillator.

6. A training device according to claim 1, in which the space is provided in a face of a cylindrical housing.

7. A training device according to claim 1, in which the space is sized to form a fit around the defibrillator function emulation device.

8. A training device according to claim 1, in which the space comprises a recess for partial receipt of the defibrillator function emulation device.

9. A training device according to claim 1, in which the space comprises a slot for substantially full receipt of the defibrillator function emulation device.

10. A training device according to claim 1, in which the housing provides a space for at least partial receipt of the emulation electrodes for attachment of the emulation electrodes to the housing.

11. A training device according to claim 10, in which the space is provided in a wall of a cylindrical housing.

12. A training device according to claim 10, in which the space comprises a recess for partial receipt of the emulation electrodes.

13. A training device according to claim 10, in which the space comprises a slot for substantially full receipt of the emulation electrodes.

14. A training device according to claim 1, in which the housing comprises a lid movable between a closed position covering the defibrillator function emulation device and the emulation electrodes and an open position revealing the defibrillator function emulation device and the emulation electrodes.

15. A training device according to claim 1, in which the housing comprises a lid movable between a closed position covering the defibrillator function emulation device and an open position revealing the defibrillator function emulation device.

16. A training device according to claim 1, in which the housing comprises a lid movable between a closed position covering the emulation electrodes and an open position revealing the emulation electrodes.

17. A training device according to claim 1, in which the emulation electrodes are defibrillator electrodes.

18. A training device according to claim 1, in which the defibrillator function emulation device is configured to emulate a predefined subset of functions of the defibrillator comprising any of a defibrillator activation function, a defibrillator status function, a defibrillator ECG measurement function, a defibrillator impedance measurement function, a defibrillator cardiac analysis function, a defibrillator cardiac diagnosis function, and a defibrillator user instruction function.

19. A training device according to claim 1, in which the defibrillator function emulation device is any of a smart phone or a tablet.

20. A method of operating a training device for training how to operate a defibrillator, the method comprising:
displaying first data on a display screen of a defibrillator function emulation device, the defibrillator function emulation device configured in a housing which imitates a shape of the defibrillator;
issuing second data from a speaker configured on the defibrillator function emulation device, the defibrillator function emulation device attached to the housing in a space configured within the housing and configured to emulate via software simulation a predefined subset of functions of the defibrillator, wherein the housing comprises one or more inserts to change a size of the space to accommodate differently-sized defibrillator function emulation devices; and
emulating a defibrillator treatment function in which a shock production through emulation electrodes is simulated, wherein the emulation electrodes are attached to the housing and wherein the training device does not contain any component capable of being charged to provide a defibrillation shock.

* * * * *